United States Patent
Ogawa et al.

(10) Patent No.: US 7,812,181 B2
(45) Date of Patent: Oct. 12, 2010

(54) PROCESS FOR PRODUCING GLYCOLIDE AND GLYCOLIC ACID OLIGOMER FOR PRODUCTION OF GLYCOLIDE

(75) Inventors: Tomoyuki Ogawa, Fukushima-Ken (JP); Masaru Kagoshima, Fukushima-Ken (JP)

(73) Assignee: Kureha Corporation, Tokyo (JP)

( * ) Notice: Subject to any disclaimer, the term of this patent is extended or adjusted under 35 U.S.C. 154(b) by 335 days.

(21) Appl. No.: 11/808,854

(22) Filed: Jun. 13, 2007

(65) Prior Publication Data

US 2007/0293653 A1 Dec. 20, 2007

(30) Foreign Application Priority Data

Jun. 19, 2006 (JP) .............................. 2006-168588

(51) Int. Cl.
*C07D 319/12* (2006.01)
*C08F 301/00* (2006.01)

(52) U.S. Cl. ........................ 549/274; 524/765; 524/766; 525/450; 560/185

(58) Field of Classification Search ................. 549/274; 528/361

See application file for complete search history.

(56) References Cited

U.S. PATENT DOCUMENTS 7,235,673 B2 * 6/2007 Yamane et al. .............. 549/274

OTHER PUBLICATIONS

DuPont product specification sheet—Glycolic Acid 70% Technical Solution.*
DuPont product specification sheet—Glycolic Acid 70% Solution High Purity.*

* cited by examiner

*Primary Examiner*—Randy Gulakowski
*Assistant Examiner*—Rachel Kahn
(74) *Attorney, Agent, or Firm*—Wenderoth, Lind & Ponack, LLP

(57) ABSTRACT

Glycolide production through depolymerization of glycolic acid oligomer is stabilized by controlling impurities in the glycolic acid oligomer to allow economical and effective production of glycolide. More specifically, the depolymerization system is controlled to suppress an effective concentration (x+100y wt. %) of depolymerization-obstructing substances calculated as a total of a concentration calculated as diglycolic acid (of x wt. %) of hydroxyl group-free impurity carboxylic acids (A) and 100 times a concentration calculated as ammonia (of y wt. %) of nitrogen-containing substances (B), respectively with respect to the starting glycolic acid oligomer in the depolymerization system, to at most 15 wt. %.

10 Claims, No Drawings

PROCESS FOR PRODUCING GLYCOLIDE AND GLYCOLIC ACID OLIGOMER FOR PRODUCTION OF GLYCOLIDE

FIELD OF THE INVENTION

The present invention relates a commercially useful process for producing glycolide which is a cyclic dimer ester of glycolic acid, and a glycolic acid oligomer used as a starting material in the process.

RELATED BACKGROUND ART

Glycolide is useful as a starting material for production of polyglycolic acid which is a resin material excellent in hydrolyzability in living things or in the earth and also excellent in gas-barrier property. More specifically, polyglycolic acid is a polymer having a recurring unit of —($-CH_2-CO-O-$)— obtained by dehydro-polycondensation of glycolic acid (i.e., α-hydroxyacetic acid), but according to this process, it is difficult to obtain polyglycolic acid of a high molecular weight. Accordingly, a process of ring-opening polymerization of glycolide ($CH_2-CO-O$)$_2$ which is a cyclic dimer ester of glycolic acid to obtain a high-molecular weight polyglycolic acid, is advantageous (Patent document 1 listed below).

In order to produce polyglycolic acid from glycolide as a starting monomer on a commercial scale, it is indispensable to supply high-purity glycolide economically. Glycolide is a cyclic ester formed by elimination of two water molecules from two molecules of glycolic acid, but esterification of glycolic acid generally results in oligomers and fails to provide glycolide. Instead thereof, a process of de-polymerizing the thus-formed glycolic acid oligomer to produce glycolide is well known.

However, commercially produced glycolic acid oligomer contains various impurities which are presumably principally attributable to glycolic acid production process, and these impurities are known to exert adverse effects to the depolymerization of glycolic acid for producing glycolide.

For example, our research group has clarified that hydrolysis of glycolic acid oligomer formed by polycondensation (esterification) of commercially available glycolic acid aqueous solution results in glycolic acid accompanied with a small amount of impurity carboxylic acids not having hydroxyl group, such as diglycolic acid, methoxyacetic acid and oxalic acid. Herein, "impurity carboxylic acids" mean carboxylic acids regarded as impurities of glycolic acid (which are likely to accompany glycolic acid but are not convertible into glycolide). Based on the knowledge, our research group has developed a glycolide production process wherein a starting glycolic acid oligomer with a reduced amount of such impurity carboxylic acids is used in order to exclude adverse effects thereof to glycolide production (Patent document 2 below), and a glycolide production process wherein an alcoholic hydroxyl group-containing compound is caused to be co-present in the depolymerization system in order to reduce adverse effects of such impurity carboxylic acids during the depolymerization (Patent document 3 below).

However, commercially produced glycolic acid oligomer further contains various impurities principally attributable to the glycolic acid production process in addition to the above-mentioned impurity carboxylic acids.

For example, the above-mentioned impurity carboxylic acids, such as diglycolic acid, methoxyacetic acid and oxalic acid are impurities generally contained in glycolic acid obtained by carboxylation of formalin with carbon dioxide in the presence of an acid catalyst (the high-pressure process, e.g., Patent document 4 below), but the process of purification thereof by using an ion exchange resin ("IRA-68", as disclosed in Patent document 5 below) can result in contamination with a nitrogen-containing substance such as amino group. Indeed, nitrogen-containing substances have been detected in commercially available glycolic acid aqueous solution.

Further, according to a glycolic acid production process by hydrolysis of glycolonitrile known to result in less impurity carboxylic acids (e.g., Patent document 6 below) can result in contamination with more nitrogen-containing substances in the product glycolic acid.

Accordingly, glycolic acid oligomer obtained by polycondensation of glycolic acid obtained in the above-described manner can contain nitrogen-containing substances as described above in addition to the impurity carboxylic acids.

However, the effect of such nitrogen-containing substances in glycolide production by depolymerization of glycolic acid oligomer has not been known.

Patent document 1: WO2005/044894A1
Patent document 2: JP2002-114775A
Patent document 4: JP2004-523596A
Patent document 3: U.S. Pat. No. 2,152,852
Patent document 5: U.S. Pat. No. 3,859,349
Patent document 6: JP62-267257A
Patent document 7: WO2006/064611A1

DISCLOSURE OF INVENTION

A principal object of the present invention is to provide a commercially useful process for producing glycolide according to depolymerization of glycolic acid oligomer having paid more general consideration to adverse effects of impurities in the glycolic acid oligomer, as an invention of improvement to the inventions of the above-mentioned Patent documents 2 and 3.

According to our study, impurities contained in commercially produced glycolic acid oligomer include not only the above-mentioned impurity carboxylic acids but also nitrogen-containing substances, such as amines, ammonium salts and amides, which exert adverse effects, such as lowering in reaction velocity and viscosity increase of the system, to the depolymerization of glycolic acid oligomer in the presence of an organic solvent, equally as or more than the above-mentioned impurity carboxylic acids. More specifically, it has been confirmed that nitrogen-containing substances in an amount calculated as ammonia have an retarding effect to depolymerization of glycolic acid oligomer as ca. 100 times as much as the impurity carboxylic acids in an amount calculated as diglycolic acid and also exhibit an adverse effect due to viscosity increase of the liquid in the reaction system.

Based on the above-mentioned knowledge, according to the present invention, there is provided: a process for producing glycolide, comprising: feeding starting glycolic acid oligomer repetitively and/or continuously into a depolymerization system containing an organic solvent and depolymerizing the glycolic acid oligomer under heating to produce glycolide, wherein the depolymerization system is controlled to suppress an effective concentration (x+100y wt. %) of depolymerization-obstructing substances calculated as a total of a concentration calculated as diglycolic acid (of x wt. %) of hydroxyl group-free impurity carboxylic acids (A) and 100 times a concentration calculated as ammonia (of y wt. %) of nitrogen-containing substances (B), respectively with respect to the starting glycolic acid oligomer in the depolymerization system, to at most 15 wt. %.

According to the present invention, there is further provide: a glycolic acid oligomer for production of glycolide, having an effective concentration (x+100y wt. %) of depolymerization-obstructing substances calculated as a total of a concentration calculated as diglycolic acid (of x wt. %) of hydroxyl group-free impurity carboxylic acids (A) and 100 times a concentration calculated as ammonia (of y wt. %) of nitrogen-containing substances (B), respectively with respect to the glycolic acid oligomer, of at most 10 wt. %.

BEST MODE FOR PRACTICING THE INVENTION (1) Depolymerization

The present invention adopts a solution depolymerization mode for depolymerization of glycolic acid oligomer effected in a solution phase containing an organic solvent from the viewpoints of suppressing the conversion of the glycolic acid oligomer into heavier products and efficiency of glycolide formation.

The glycolide formation according to the solution depolymerization may be performed, e.g., by heating a mixture including glycolic acid oligomer and a polar organic solvent having a boiling point of 230-450° C. and a molecular weight of 150-450 to dissolve the oligomer in the organic solvent until the remaining ratio of the molten phase thereof is lowered to at most 0.5, continuing the heating at a temperature causing the depolymerization of the oligomer under normal pressure or a reduced pressure to depolymerize the oligomer, distilling off the resultant glycolide together with the organic solvent and recovering the organic solvent and glycolide in separation from the distillate liquid.

In the present invention, the step of depolymerization by adding glycolic acid oligomer and organic solvent to the remaining reaction liquid is repeated or performed continuously.

More specifically, while the organic solvent and glycolide are recovered in separation from the distillate liquid, the starting glycolic acid oligomer and organic solvent are added to the remaining reaction liquid to effect the depolymerization continuously, or after the organic liquid and glycolide are recovered in separation from the distillate liquid, the starting glycolic acid oligomer and organic solvent are added to all or a part of the remaining reaction liquid to repeat the depolymerization.

(2) Glycolic Acid Oligomer

The glycolic acid oligomer used in the present invention may be obtained by condensing glycolic acid, or an ester or salt thereof. More specifically, glycolic acid or an ester or salt thereof is heated to a temperature of 100-250° C., preferably 140-230° C., optionally in the presence of a condensation catalyst or a transesterification catalyst to effect the condensation or transesterification until the distillation of low-molecular weight substances, such as water or alcohol, is substantially completed. After completion of the condensation or transesterification, the resultant oligomer can be used as it is as the starting material of the production process of the present invention. Alternatively, the oligomer can be used as the starting material after being washed with a non-solvent, such as benzene or toluene, to remove the non-reacted material, lower-degree polymerizates, catalyst, etc. The oligomer can be either cyclic or linear. The degree of polymerization is not particularly restricted, but the melting point (TM) thereof may preferably be at least 140° C., more preferably at least 160° C., further preferably at least 180° C. Herein, Tm refers to a melting point detected at a temperature-increasing rate of 10° C./min. in an inert gas atmosphere by using a differential scanning calorimeter.

As discussed above, such glycolic acid oligomer may contain hydroxyl group-free impurity carboxylic acids (A), such as diglycolic acid, methoxyacetic acid and oxalic acid, and nitrogen-containing substances (B), such as ammonium salts, glycoloamide and amides, in different ratios, principally depending on the process for producing the glycolic acid or an ester or salt thereof (hereinafter sometimes referred to as "glycolic acid, etc." used as the starting material. A portion of these impurities is distilled together with glycolide as the objective product and the organic solvent out of the solution depolymerization system and separated from the glycolide and organic solvent in a subsequent purification step, but the remainder of the impurities remain and accumulate in the depolymerization system to lower the depolymerization speed and be changed into heavier substances to increase the viscosity of the system, thereby making difficult the effective and stable continuation of depolymerization. Furthermore, even the distilled portion of impurities may be accumulated in the depolymerization system, if the residue from the purification system is recycled to the depolymerization system in order to recover glycolide from the residue.

Accordingly, in the present invention, while noting principally the depolymerization-obstructing effect of these impurities, an effective concentration (x+100y wt. %) of depolymerization-obstructing substances calculated as a total of a concentration calculated as diglycolic acid (of x wt. %) of hydroxyl group-free impurity carboxylic acids (A) and 100 times a concentration calculated as ammonia (of y wt. %) of nitrogen-containing substances (B), respectively with respect to the starting glycolic acid oligomer in the depolymerization system, is controlled to be at most 15 wt. %, preferably at most 12 wt. %, further preferably at most 6 wt. %. The effective concentration of depolymerization-obstructing substances is preferably as low as possible, but it is generally difficult to lower the effective concentration to below 0.01 wt. %.

The impurity carboxylic acids (A) and nitrogen-containing substances (B) in the glycolic acid oligomer are contained in glycolic acid, etc., used as the starting material for production of glycolic acid oligomer, in different proportions depending on its production process (e.g., the high-pressure process, the nitrile process, etc., discussed above) and tend to be accumulated in the glycolic acid oligomer depolymerization system in many cases. Accordingly, in order to lower the concentrations of these impurities in the depolymerization system, in a preferred embodiment of the present invention, an effective concentration (x+100y wt. %) of depolymerization-obstructing substances calculated as a total of a concentration calculated as diglycolic acid (of x wt. %) of hydroxyl group-free impurity carboxylic acids (A) and 100 times a concentration calculated as ammonia (of y wt. %) of nitrogen-containing substances (B), in the glycolic acid oligomer as the starting material, is controlled to be at most 10 wt. %, preferably at most 8 wt. %, more preferably at most 5 wt. %. The effective concentration of depolymerization-obstructing substances is preferably as low as possible, but it is generally difficult to lower the effective concentration to below 0.007 wt. %.

In order to reduce the impurity concentrations in glycolic acid oligomer, it is desirable to reduce the impurity concentrations in glycolic acid, etc., as the starting material for production of the glycolic acid oligomer. This is because, while various methods are known for reducing impurities in organic compounds, it is difficult to apply any known impurity reduction methods directly to glycolic acid oligomer which already contain a multiplicity of principal components to attain effective function of the methods.

More specifically, for the purpose of lowering the impurity concentrations in glycolic acid, etc., as the starting material for production of glycolic acid oligomer, it is possible to apply an impurity reduction method, such as reduction by crystallization, reduction by an ion exchange resin, reduction by electrical dialysis, reduction by solvent extraction, reduction of nitrogen-containing impurities by esterification of glycolic acid with an alcohol followed by distillation purification and restoration to glycolic acid, etc. Depending on the contents of the impurity carboxylic acids (A) and the nitrogen-containing substances (B) as the impurities, these impurity methods may be selected singly or in combination of plural methods, or it is possible to mix such glycolic acid, etc., with purified glycolic acid for dilution of the impurities to achieve a lowering to a prescribed concentration or below. Among these, it is particularly effect to apply a crystallization method of Patent document 7 (WO2006/064611A1) developed by our research group, i.e., a process for purifying a hydroxycarboxylic acid, comprising: a crystallization step of subjecting a hydroxycarboxylic acid aqueous solution (as represented by a glycolic acid aqueous solution) to crystallization for purification, a separation step of separating a hydroxycarboxylic crystal from a mother liquid, and a washing step of washing the hydroxycarboxylic acid for further purification with a washing liquid, wherein the washing liquid is a hydroxycarboxylic acid aqueous solution. Preferably, the washing step is performed by using a solid-liquid separator (more preferably, a centrifuge) having a washing facility. The disclosure of the WO publication is incorporated herein by reference. The crystallization method of the WO publication has been principally developed as a method for reducing the impurity carboxylic acids (A) in glycolic acid, but the method has been found also very effective for reducing the nitrogen-containing substances (B) according to our study.

It is true that the impurities in glycolic acid, etc., as a starting material for production of glycolic acid oligomer which in turn is the starting material for production of glycolide according to the present invention, is preferably as small in amount as possible. However, glycolic acid is such a material as to cause esterification to form oligomers due to a heating step which is inevitably included to some extent in any impurity reduction method, and excessive purification thereof is not preferable since it is accompanied with a lowering in yield and an increase in production cost. Accordingly, it is preferred appropriately to reduce the impurities in glycolic acid, etc., as a starting material of glycolic acid oligomer to use glycolic acid oligomer containing controlled amounts of impurity carboxylic acids (A) and nitrogen-containing substances (B) while grasping the degree of adverse effects of the impurities (A) and (B) to glycolide production, for depolymerization to produce glycolide according to the present invention.

Polar Organic Solvent

Glycolide production according to the process of the present invention is performed by depolymerization of glycolic acid oligomer in a polar organic solvent.

The polar organic solvent is used as a solvent for depolymerization and also for taking out the resultant glycolide from the depolymerization system. The polar organic solvent may desirably have a boiling point in the range of 230-450° C. and a molecular weight in the range of 150-450.

If the boiling point of the solvent is below 230° C., it becomes impossible to set a high depolymerization temperature so that the glycolide production speed is lowered. On the other hand, if the boiling point of the solvent exceeds 450° C., the distillation of the solvent becomes difficult so that the co-distillation with the glycolide formed by depolymerization becomes difficult. The boiling point is preferably in the range of 235-450° C., more preferably 260-430° C., most preferably 280-420° C.

Too small and too large a molecular weight of the polar organic solvent are both undesirable since the co-distillation with glycolide becomes difficult thereby. The molecular weight may preferably be in the range of 180-420, more preferably 200-400.

Examples of the polar organic solvent may include: aromatic dicarboxylic acid diesters, aliphatic dicarboxylic acid diesters, and polyalkylene glycol diethers. More specifically, examples of the aromatic dicarboxylic acid diesters may include: phthalic acid esters, such as dibutyl phthalate, dioctyl phthalate, dibenzyl phthalate and benzyl butyl phthalate, and benzoic acid esters, such as benzyl benzoate.

Examples of the aliphatic dicarboxylic acid diesters may include: adipic acid esters, such as octyl adipate, and sebacic acid esters, such as dibutyl sebacate.

The polyalkylene glycol diethers which are used as a solvent for depolymerization and suitably used as a solvent for taking the resultant glycolide out of the reaction system in the present invention are compounds represented by the following structural formula (1):

$$X^2O\text{—}(\text{—}R^3\text{—}O\text{—})_r\text{—}Y \tag{1},$$

wherein $R^3$ denotes a methylene group or a linear or branched alkylene group having 2-8 carbon atoms; $X^2$ and Y denote a hydrocarbon group and r is an integer of at least 1. In the case of r being 2 or more, a plurality of $R^3$ may be the same or different.

Examples of the polyalkylene glycol diethers may include: polyethylene glycol dialkyl ethers, such as diethylene glycol dibutyl ether, diethylene glycol dihexyl ether, diethylene glycol dioctyl ether, triethylene glycol dimethyl ether, triethylene glycol diethyl ether, triethylene glycol dipropyl ether, triethylene glycol dibutyl ether, triethylene glycol dihexyl ether, triethylene glycol dioctyl ether, tetraethylene glycol dimethyl ether, tetraethylene glycol diethyl ether, tetraethylene glycol dipropyl ether, tetraethylene glycol dibutyl ether, tetraethylene glycol dihexyl ether, tetraethylene glycol dioctyl ether, diethylene glycol butyl hexyl ether, diethylene glycol butyl octyl ether, diethylene glycol hexyl octyl ether, triethylene glycol butyl hexyl ether, triethylene glycol butyl octyl ether, triethylene glycol hexyl octyl ether tetraethylene glycol butyl hexyl ether, tetraethylene glycol butyl octyl ether, and tetraethylene glycol hexyl octyl ether; polyalkylene glycol dialkyl ethers, inclusive of polypropylene glycol dialkyl ethers and polybutylene glycol dialkyl ethers formed by substituting propyleneoxy group and butyleneoxy group, respectively, for the ethyleneoxy group in the polyethylene glycol dialkyl ethers; polyalkylene glycol alkyl aryl ethers, inclusive of diethylene glycol butyl phenyl ether, diethylene glycol hexyl phenyl ether, diethylene glycol octyl phenyl ether, triethylene glycol butyl phenyl ether, triethylene glycol hexyl phenyl ether, triethylene glycol octyl phenyl ether, tetraethylene glycol butyl phenyl ether, tetraethylene glycol hexyl phenyl ether, tetraethylene glycol octyl phenyl ether, polyethylene glycol alkyl aryl ethers, formed by substituting alkyl, alkoxy, halogen, etc., for a hydrogen group in the phenyl group of the above compounds, polypropylene glycol alkyl aryl ethers, and polybutylene glycol alkyl aryl ethers formed by substituting propyleneoxy group and butyleneoxy group for the ethyleneoxy group of the above compounds; and polyalkylene glycol diaryl ethers, inclusive of diethylene glycol diphenyl ether, triethylene glycol diphenyl ether, tetraethylene glycol diphenyl ether, polyethylene glycol diaryl ethers formed by substituting alkyl, alkoxy, halogen, etc., for the phenyl group of the above compounds, and polypropylene glycol diaryl ethers and polybutylene glycol diaryl ethers formed by substituting propyleneoxy group and butyleneoxy group for the ethyleneoxy group of the above compounds.

These polar organic solvents may be used in an amount of ordinarily 0.3-50 times, preferably 0.5-20 times, more preferably 1-10 times, by weight with respect to the glycolic acid oligomer.

(4) Compound having Alcoholic Hydroxyl Group

In order to reduce the adverse effect of the impurity carboxylic acids (A), it is also preferred to effect the depolymerization in a state where a compound having an alcoholic hydroxyl group (C) is always co-present in at least a prescribed amount in the reaction system. The manner of addition of the compound having an alcoholic hydroxyl group (C) into the reaction system is not particularly restricted.

For example it is possible to add a necessary amount of the compound having an alcoholic hydroxyl group (C) at the same time as or before or after the charging of the starting glycolic acid oligomer. Alternatively, it is also possible that an excessive amount of the compound (C) is added in advance, and then starting glycolic acid oligomer is added repeatedly or continuously to effect depolymerization, while thereafter adding the compound (C) little by little or in some amount stepwise before the total amount of the impurity carboxyl groups is accumulated in excess of a prescribed amount with respect to the amount of the alcoholic hydroxyl group of the compound (C) in the reaction system.

In the case of solution depolymerization, it is possible to use a solution formed by dissolving glycolic acid oligomer and a prescribed amount of the compound (C) having an alcoholic hydroxyl group in a polar organic solvent for the purpose of adding a necessary amount of the compound (C) into the reaction system. It is preferred that the compound (C) having an alcoholic hydroxyl group is added so as to provide at least a prescribed amount (at least 0.5 equivalent) of alcoholic hydroxyl group with respect to the total amount of the carboxyl group as the impurity component in the depolymerization system after the addition (measured after hydrolysis under an alkaline condition of a portion of the contents in the depolymerization system). Practically, it is convenient to measure a total amount of carboxyl group contained in the starting glycolic acid oligomer in advance and adjust the amount of the alcoholic hydroxyl group to 0.5-1.5 equivalent, preferably 0.8-1.2 equivalent, further preferably 0.9-1.1 equivalent, with respect to the total amount of carboxyl group. Below 0.5 equivalent, the amount of the alcoholic hydroxyl group in the reaction system is lowered so that it becomes difficult to attain the effect of suppressing the lowering of glycolide formation speed. On the other hand, the addition amount in excess of 1.5 equivalent does not increase the effect.

Examples of the compound (C) having an alcoholic hydroxyl group may include: monohydric and polyhydric alcohols (inclusive of partially esterified products and partially etherified products) and phenols. Alcohols are most effective as the compound (C) having an alcoholic hydroxyl group, and particularly a polyhydric alcohol having two or more hydroxyl groups in its molecule is preferred. Such a polyhydric alcohol has an advantage of a high boiling point even at a low molecular weight so that it is not readily distilled out of the reaction system, and even a smaller amount of addition thereof can exhibit an excellent effect compared with a monohydric alcohol. The compound (C) may preferably have a boiling point of at least 190° C., more preferably at least 195° C.

In case where the compound (C) having an alcoholic hydroxyl group is distilled out of the system to some extent, it is preferred to supplement the compound (C) commensurate with the distilled amount.

Among the alcohols, it is possible to suitably use a polyalkylene glycol represented by formula (2) below:

(wherein $R^1$ denotes a methylene group or a linear or branched alkylene group having 2-8 carbon atoms, and p is an integer of at least 1. In case where p is 2 or larger, plural groups $R^1$ may be the same or different), a polyalkylene glycol monomethyl ether represented by formula (3) below:

(wherein $R^2$ denotes a methylene group or a linear or branched alkylene group having 2-8 carbon atoms, $X^1$ denotes a hydrocarbon group, and q is an integer of at least 1. In case where q is 2 or larger, plural groups $R^2$ may be the same or different), or glycerin, tridecanol, ethylene glycol, hexamethylene glycol, decane diol, etc.

Specific examples of the polyalkylene glycol may include: polyethylene glycol, polypropylene glycol and polybutylene glycol.

Specific examples of the polyalkylene glycol monoether may include: polyethylene glycol monoalkyl ethers, such as polyethylene glycol monopropyl ether, polyethylene glycol monobutyl ether, polyethylene glycol monohexyl ether, polyethylene glycol monooctyl ether, polyethylene glycol monodecyl ether, polyethylene glycol monolauryl ether; and polypropylene glycol monoalkyl ethers and polybutylene glycol monoalkyl ethers formed by substituting propyleneoxy group and butyleneoxy group, respectively, for the ethyeneoxy group in the above polyethylene glycol monoalkyl ethers.

The above-mentioned compounds as examples of the compound (C) having an alcoholic hydroxyl group may be used singly or in mixture of two or more species, or can also be co-used together with glycolic acid oligomer formed by co-condensation with a compound having an alcoholic hydroxyl group.

Recovery of Glycolide

Glycolide in the distilled liquid from the depolymerization system may be separated from the polar organic solvent, e.g., by reduced pressure distillation, followed by a purification step, such as crystallization, to be recovered in a purified form, and may for example be used as a starting material for polymerization to provide polyglycolic acid.

Continuation and Termination of Depolymerization

The depolymerization reaction may be continued by successively supplying the polar organic solvent and glycolic acid oligomer (and optionally the compound (C) having an alcoholic hydroxyl group commensurate in amount with the accumulated impurity carboxylic acids (A)) in amounts commensurate with the distilled organic solvent and glycolide. Alternatively, the depolymerization may be performed batchwise, and to all or a portion of the remaining liquid, the starting glycolic acid oligomer and polar organic solvent (and optionally compound (C) having an alcoholic hydroxyl group commensurate in amount with the accumulated carboxylic acids (A)) may be added to repeat the depolymerization. Along with the continuation or repetition of the depolymerization, the lowering in depolymerization speed due to accumulation of a portion of the nitrogen-containing substances (B) and the impurity carboxylic acids (A) in the system and also the viscosity increase in the system due to formation of heavier products from a portion of the nitrogen-containing substances (B) and the impurity carboxylic acids (A) can occur, so that the depolymerization may be continued by withdrawing a portion of the liquid in the system, or the depolymerization may be once terminated by judging from the lowering in glycolide distillation speed and the liquid in the system is refreshed to resume the depolymerization.

EXAMPLES

Hereinbelow, the present invention will be described more specifically based on Synthesis Examples, Examples and Comparative Examples, but the scope of the present invention is not restricted to those Examples. The description herein including the following is based on the results of the following measurement.

(Analysis of Impurities)

Glycolic acid aqueous solution, glycolic acid oligomer and samples taken from depolymerization system were subjected to formulation of samples depending on the contents of analyses and then subjected to respective analyses.

(1) Analysis of Glycolic Acid, Methoxyacetic Acid and Oxalic Acid.

A sample in an amount of 5.8 g was weighed in a 200 ml —beaker, and 4 g of NaOH and 40 g of distilled water were added thereto, followed by stirring for 12-48 hours at 40° C. to effect complete hydrolysis. The hydrolysis liquid was adjusted to pH4.7 with sulfuric acid and distilled water was added until the total amount reached 80 g. Then, 2 g of the thus formed testing liquid was further diluted to 50 ml with distilled water to provide an analysis sample.

The analysis sample was analyzed by high-performance liquid chromatography (HPLC) under the following conditions:
Conditions for analysis by HPLC)
Apparatus: "L-6020", made by K.K. Hitachi Seisakusho
Column: "Intersil ODS-3V" (5 μm), 250×4.6 mm I.D.
Flow rate: 1.0 mL/min.
Elution liquid: 0.1M-ammonium dihydrogenphosphate+ phosphoric
acid aqueous solution (pH2.5)
Oven temperature: 40° C.
Detection condition: UV 210 nm.

(2) Analysis of Glycoloamide

An analysis sample was prepared in the same manner as in (1) above except for diluting 4 g of the testing liquid instead of the 2 g of the testing liquid to 50 ml with distilled water to provide an analysis sample, which was then analyzed by HPLC in the same manner as in (1) above.

(3) Analysis of Ammonia

An analysis sample was prepared in the same manner as in (1) above except for diluting 4 g of the testing liquid instead of the 2 g of the testing liquid to 50 ml with distilled water to provide an analysis sample, which was then analyzed by ion chromatography (IC) under the following conditions:
(Conditions for analysis by IC)
Apparatus: "DX-500", made by Nippon Dionex K.K.
Column: "DIONEX IONPAC CS-12A"
Flow rate: 1.0 mL/min.
Elution liquid: 20 mM-methane-sulfonic acid
Detection means: Electroconductivity (4) Analysis of Total Nitrogen Glycolic acid aqueous solution, glycolic acid oligomer and samples taken from depolymerization system were used as they were as analysis samples and analyzed by pyrochemical emission analysis under the following conditions:

(Conditions for pyrochemical emission analysis)
Apparatus: "ANTEK MODEL9000", made by Astec K.K.
Temperature: 1100° C.
Detection means: Photoelectron multiplier From the concentration ($x_1$ wt. %) of diglycolic acid (M.W. (molecular weight)=134), the concentration ($x_2$ wt. %) of methoxyacetic acid (M.W.=90) and the concentration ($x_3$ wt. %) of oxalic acid (M.W.=90) with respect to the glycolic acid oligomer, respectively measured in the above-described manner, the total concentration calculated as diglycolic acid (x wt. %) of the impurity carboxylic acids (A) was calculated according to the following formula:

$$x = x_1 + (134/90)x_2 + (134/90)x_3.$$

On the other hand, the concentration calculated as ammonia (M.W.=17) of nitrogen-containing substances was calculated from the total concentration ($y_1$ wt. %) of nitrogen (atomic weight=14) measured in a manner as described in the above (4) according to the following formula:

$$y = y_1 \times (17/14).$$

From the above-calculated concentrations x and y, the effective concentration (=(x+100y) wt. %) of depolymerization-obstructing substances was calculated with respect to a starting glycolic acid oligomer and a sample taken from the depolymerization system, respectively.

(Purification of Glycolic Acid)

A commercially available ca. 70%-conc. glycolic acid aqueous solution, after sample preparation, was analyzed in the above-described manner to provide results on the weight basis of total glycolic acid 70%, diglycolic acid 0.04%, methoxyacetic acid 2.2%, total nitrogen 22 ppm, ammonia 16 ppm (ca. 60% of the total nitrogen) and glycoloamide: below detection limit (=100 ppm).

The above-mentioned commercially available glycolic acid aqueous solution was subjected to 19 cycles of batchwise purification operations of which each cycle included unit operations of (1) dehydration, (2) crystallization, (3) solid-liquid separation and washing of crystal and recycle of the filtrate liquid, according to the method described in Example 1 of WO2006/064611 A1 (Patent document 7). As a result, after final concentration adjustment by adding pure water, there was obtained a high-purity glycolic acid aqueous solution containing on the weight basis: total glycolic acid 70%, diglycolic acid 0.04%, methoxyacetic acid 0.3%, total nitrogen 1 ppm, ammonia: below detection limit (=10 ppm) and glycoloamide: below detection limit (=100 ppm).

Synthesis Example 1

Synthesis of Glycolic Acid Oligomer (a)

Into a 500 ml-glass-made vessel, 800 g of the above-obtained high-purity glycolic acid aqueous solution was charged and heated up to 200° C. under stirring at normal pressure to proceed with condensation while distilling out resultant water. Then, the pressure in the vessel was lowered to 5.0 kPa and held at 200° C. for 2 hours to distill off low-boiling point fractions including non-reacted glycolic acid, thereby preparing 400 g of glycolic acid oligomer (a) containing impurity carboxylic acids (A) at a concentration calculated as diglycolic acid (x) of 0.16 wt. % and nitrogen-containing substances (B) at a concentration calculated as ammonia (y) of 0.0002 wt. % giving an effective concentration (x+100y) of depolymerization-obstructing substances of 0.18 wt. %.

Synthesis Example 2

Synthesis of Glycolic Acid Oligomer (b)

A solution was prepared by adding glycoloamide (made by Aldrich Co.) so as to provide a concentration of 0.1 wt. % to the above-prepared high-purity glycolic acid aqueous solution. The procedure of Synthesis Example 1 was repeated except for using the solution instead of the high-purity glycolic acid aqueous solution per se to obtain glycolic acid oligomer (b). The nitrogen content in glycoloamide is 19 wt. % so that 0.1 wt. % of glycoloamide correspond to 0.02 wt. % of ammonia on an equi-molar basis, and it was multiplied by a condensation ratio of 2(=800 g/400 g) to provide a nitrogen content calculated as ammonia in the oligomer (b) of 0.04%. Thus, the glycolic acid oligomer (b) contained impurity carboxylic acids (A) at a concentration calculated as diglycolic acid (x) of 0.16 wt. % and nitrogen-containing substances (B) at a concentration calculated as ammonia (y) of 0.04 wt. % giving an effective concentration (x+100y) of depolymerization-obstructing substances of 4.4 wt. %.

Synthesis Example 3

Synthesis of Glycolic Acid Oligomer (c)

The procedure of Synthesis Example 1 was repeated except for using the above-mentioned commercially available glycolic acid aqueous solution instead of the high-purity glycolic acid aqueous solution to obtain glycolic acid oligomer (c) containing impurity carboxylic acids (A) at a concentration calculated as diglycolic acid (x) of 10.6 wt. % and nitrogen-containing substances (B) at a concentration calculated as ammonia (y) of 0.005 wt. % giving an effective concentration (x+100y) of depolymerization-obstructing substances of 11 wt. %.

Synthesis Example 4

Synthesis of Glycolic Acid Oligomer (d)

A solution was prepared by adding ammonia water (made by Kanto Kagaku K.K.) so as to provide an ammonia concentration of 0.5 wt. % to the above prepared high purity glycolic acid aqueous solution. The procedure of Synthesis Example 1 was repeated except for using the thus-prepared solution instead of the high-purity glycolic acid aqueous solution per se to obtain glycolic acid oligomer (d) containing impurity carboxylic acids (A) at a concentration calculated as diglycolic acid (x) of 0.16 wt. % and nitrogen-containing substances (B) at a concentration calculated as ammonia (y) of 0.93 wt. % giving an effective concentration (x+100y) of depolymerization-obstructing substances of 94 wt. %.

Synthesis Example 5

Synthesis of Glycolic Acid Oligomer (e)

A solution was prepared by adding ammonia water (made by Kanto Kagaku K.K.) so as to provide an ammonia concentration of 0.1 wt. % to the above prepared high purity glycolic acid aqueous solution. The procedure of Comparative Example 1 was repeated except for using the thus-prepared solution instead of the high-purity glycolic acid aqueous solution per se to obtain glycolic acid oligomer (e). The thus-prepared glycolic acid oligomer (e) was subjected to the pyrochemical luminescence analysis to exhibit a total nitrogen content of 0.19 wt. %. The oligomer (e) was recovered at a rate of 50 wt. % with respect to the charged glycolic acid, thus having been concentrated at a ratio of 2 times. On the other hand, the total distillate liquid was subjected to pyrochemical luminescence analysis to exhibit a total nitrogen content calculated as ammonia of 7.5 mg, which corresponded to 0.9 wt. % of the charged 800 mg of ammonia. Thus, substantially all the amount of the charged amount remained in the oligomer. The glycolic acid oligomer (e) contained impurity carboxylic acids (A) at a concentration calculated as diglycolic acid (x) of 0.16 wt. % and nitrogen-containing substances (B) at a concentration calculated as ammonia (y) of 0.19 wt. % giving an effective concentration (x+100y) of depolymerization-obstructing substances of 19 wt. %.

Synthesis Example of Polyalkylene Glycol Ether

Commercially available polyethylene glycol dimethyl ether #250 (made by Merck Co.) was distilled to provide tetraethylene glycol dimethyl ether having a polymerization degree of 4 (hereinafter referred to as "TEGDME"), which was used as a solvent for solution depolymerization in the following Examples and Comparative Examples.

Example 1

Into a 500 ml-flask, 100 g of glycolic acid oligomer (a) obtained in Synthesis Example 1 above was charged. Further, 200 g of TEGDME was added thereto, and the system was heated up to 260° C. and was placed under a reduced pressure of 8.0 kPa. The distilled liquid was trapped by cooling with iced water. After 1 hour of the reaction, the distilled amount of glycolide reached 13 g. Thus, the distillation rate was 13 g/h. Then, a weight of the oligomer (a) corresponding to the distilled glycolide and a weight of TEGDME identical to TEGDME in the distilled liquid were added to repeat the depolymerization. As a result of 10 cycles of the repetition (charging totally 142 g of the oligomer (a)), 139 g of glycolide was recovered at an average glycolide distillation rate of 14 g/h. Further, the glycolide-producing depolymerization was repeated 25 cycles and could be repeated further.

At the time after completion of the 10th cycle (i.e., after continuation for 10 hours of the reaction), the glycolic acid oligomer in the system contained impurity carboxylic acids (A) at a concentration calculated as diglycolic acid (x) of 0.38 wt. %, and nitrogen-containing substances at a concentration calculated as ammonia (y) of 0.0004 wt. % giving an effective concentration (x+100y) of depolymerization-obstructing substances of 0.42 wt. %.

Example 2

A depolymerization test was performed in the same manner as in Example 1 except for using glycolic acid oligomer (b) as the starting oligomer. As a result, glycolide was distilled at a rate of 10 g/h on an average through continuation of 10 hours of reaction. The glycolide-producing depolymerization was repeated 25 cycles and could be repeated further.

At the time after completion of the 10th cycle (i.e., after continuation for 10 hours of the reaction), the glycolic acid oligomer in the system contained impurity carboxylic acids (A) at a concentration calculated as diglycolic acid (x) of 0.32 wt. %, and nitrogen-containing substances at a concentration calculated as ammonia (y) of 0.056 wt. % giving an effective concentration (x+100y) of depolymerization-obstructing substances of 5.9 wt. %.

Comparative Example 1

A depolymerization test was performed in the same manner as in Example 1 except for using glycolic acid oligomer (c) as the starting oligomer. During 8th cycle of repetition of depolymerization, the reaction system became viscous to cause bumping during the test, whereby the test was discontinued.

At the time of the discontinuation, the glycolic acid oligomer in the system contained impurity carboxylic acids (A) at a concentration calculated as diglycolic acid (x) of 21 wt. %, and nitrogen-containing substances at a concentration calculated as ammonia (y) of 0.01 wt. % giving an effective concentration (x+100y) of depolymerization-obstructing substances of 22 wt. %.

Comparative Example 2

A depolymerization test was performed in the same manner as in Example 1 except for using glycolic acid oligomer (d) as the starting oligomer. As a result, glycolide was distilled at a rate of 4 g/h on an average through continuation of 10 hours of reaction. The reaction liquid after the 10 hours became viscous as to cause a symptom of bumping, so that the test was discontinued thereafter.

At the time of the discontinuation, the glycolic acid oligomer in the system contained impurity carboxylic acids (A) at a concentration calculated as diglycolic acid (x) of 0.21 wt. %, and nitrogen-containing substances at a concentration calculated as ammonia (y) of 0.82 wt. % giving an effective concentration (x+100y) of depolymerization-obstructing substances of 82 wt. %.

Comparative Example 3

A depolymerization test was performed in the same manner as in Example 1 except for using glycolic acid oligomer (e) as the starting oligomer. As a result, glycolide was distilled at a rate of 5 g/h on an average through continuation of 10 hours of reaction, thus causing a substantial lowering in productivity of glycolide. Glycolide recovered after continuation of 10 hours was hydrolyzed with an alkali and analyzed by liquid chromatography, whereby glycoloamide wad detected therein.

At the time of discontinuation, the glycolic acid oligomer in the system contained impurity carboxylic acids (A) at a concentration calculated as diglycolic acid (x) of 0.22 wt. % and nitrogen-containing substances at a concentration calculated as ammonia (y) of 0.17 wt. % giving an effective concentration (x+100y) of depolymerization-obstructing substances of 17 wt. %.

As described above, according to the present invention, glycolide can be economically and effectively produced through depolymerization of glycolic acid oligomer by controlling the concentrations of impurity carboxylic acids (A) and nitrogen-containing substances (B) in the depolymerization system in combination to stabilize the depolymerization over a long period.

The invention claimed is:

1. A process for producing glycolide, comprising the steps of:
feeding a starting glycolic acid oligomer containing hydroxyl group-free impurity carboxylic acids (A) and nitrogen-containing compounds (B) selected from the group consisting of ammonia, ammonium salts, amines and amides repetitively and/or continuously into a depolymerization system containing an organic solvent,
depolymerizing the glycolic acid oligomer under heating to produce glycolide,
calculating an effective concentration (x+100y wt. %) of depolymerization-obstructing substances as a total of a concentration calculated as diglycolic acid (of x wt. %) of the hydroxyl group-free impurity carboxylic acids (A) and 100 times a concentration calculated as ammonia (of y wt. %) of the nitrogen-containing compounds (B), respectively, with respect to the starting glycolic acid oligomer in the depolymerization system, and
controlling the depolymerization system to suppress the effective concentration (x+100y wt. %) to at most 15 wt. %.

2. The process according to claim 1, wherein the starting glycolic acid oligomer has an effective concentration of depolymerization-obstructing substances of at most 10 wt. %.

3. The process according to claim 1, wherein the depolymerization system further comprises an alcoholic hydroxyl group-containing compound (C).

4. The process according to claim 3, wherein the amount of the alcoholic hydroxyl group-containing compound (C) is controlled to provide at least 0.5 equivalent of alcoholic hydroxyl groups with respect to the total amount of the carboxyl groups of the hydroxyl group-free impurity carboxylic acids (A) in the depolymerization system.

5. The process according to claim 4, wherein the hydroxyl group-containing compound (C) is at least one compound selected from the group consisting of:
(i) polyalkylene glycols represented by formula (2) below:

$$HO-(-R^1-O-)_p-H- \qquad (2),$$

wherein $R^1$ denotes a methylene group or a linear or branched alkylene group having 2-8 carbon atoms, and p is an integer of at least 1 with the proviso that when p is 2 or larger, plural groups $R^1$ may be the same or different;
(ii) polyalkylene glycol monomethyl ethers represented by formula (3) below:

$$HO-(-R^2-O-)_q-X^1- \qquad (3),$$

wherein $R^2$ denotes a methylene group or a linear or branched alkylene group having 2-8 carbon atoms, $X^1$ denotes a hydrocarbon group, and q is an integer of at least 1 with the proviso that when q is 2 or larger, plural groups $R^2$ may be the same or different;
(iii) glycerin, (iv) tridecanol ethylene glycol, (v) hexamethylene glycol and (vi) decane diol.

6. The process according to claim 1, wherein the hydroxyl group-free impurity carboxylic acids (A) comprise at least one of diglycolic acid, methoxyacetic acid and oxalic acid.

7. The process according to claim 1, wherein the starting glycolic acid oligomer has a melting point of at least 140° C.

8. The process according to claim 1, wherein the organic solvent is a polar organic solvent having a boiling point of 230-450° C. and a molecular weight of 150-450.

9. The process according to claim 8, wherein the polar organic solvent is a compound represented by the following structural formula (1):

$$X^2O-(-R^3-O-)_r-Y- \qquad (1),$$

wherein $R^3$ denotes a methylene group or a linear or branched alkylene group having 2-8 carbon atoms; $X^2$ and Y denote a hydrocarbon group and r is an integer of at least 1; with the proviso that when r is 2 or more, a plurality of $R^3$ may be the same or different.

10. The process according to claim 1, wherein the amide is glycoloamide.

* * * * *